US00PP17005P3

(12) United States Plant Patent
Abrams

(10) Patent No.: US PP17,005 P3
(45) Date of Patent: Aug. 15, 2006

(54) ***GERANIUM* PLANT NAMED 'BEKY'**

(50) Latin Name: *Pelargonium×hortorum*
Varietal Denomination: Beky

(75) Inventor: Laura B Abrams, Sudbury, MA (US)

(73) Assignee: J P Bartlett Co Inc, Sudbury, MA (US)

( * ) Notice: Subject to any disclaimer, the term of this patent is extended or adjusted under 35 U.S.C. 154(b) by 154 days.

(21) Appl. No.: 10/736,201

(22) Filed: Dec. 15, 2003

(65) Prior Publication Data

US 2005/0132457 P1 Jun. 16, 2005

(51) Int. Cl.
*A01H 5/00* (2006.01)

(52) U.S. Cl. ..... Plt./329
(58) Field of Classification Search ..... Plt./329
See application file for complete search history.

(56) References Cited

U.S. PATENT DOCUMENTS

PP15,858 P2 * 7/2005 Dummen ..... Plt./329

OTHER PUBLICATIONS

UPOV ROM GTITM Computer Database, GTI JOUVE Retrieval Software 2005/02 Citations for 'Rebecca' and 'Rebeca'.* http://www.bartlettgreenhouses.com/2004SPRINGbrochure.pdf.*

* cited by examiner

*Primary Examiner*—Kent Bell
*Assistant Examiner*—W C Haas

(57) ABSTRACT

This invention is a new and distinct cultivar of a zonal *geranium, Pelargonium×hortorum,* named 'Beky'. The cultivar has a brilliant array of colors within the plant's purple blossom and medium green foliage on a stable, full, well-branched plant.

1 Drawing Sheet

Botanical designation: *Pelargonium×hortorum.*
Variety denomination: 'Beky'.

BACKGROUND OF THE INVENTION

The cultivar was developed from a controlled breeding program conducted at the Sudbury, Mass. A non-patented cultivar designated #94362 as the male parent and a non-patented cultivar designated #2484 as the female parent were crossed in a cultivated area to create a single plant named 'Beky'. 'Beky's' plant habit is symmetrical with excellent basal branching. The new cultivar 'Beky' differs from its' male parent in color shade being darker and more vibrant. The new cultivar 'Beky' differs from its' female parent in number of petals being fewer than it's parent. The new cultivar 'Becky's' similar in color to 'Springfield Violet'. Asexual propagation of the new cultivar by cuttings at the location previously stated has shown that the unique features of this new *geranium* are stable and that the plant reproduces true to type in successive generations of asexual propagation.

SUMMARY OF THE INVENTION

The plants growth habit is compact to medium in vigor. It is a full plant that performs well in both a greenhouse and in a natural environment such as a garden. It will grow more compact under drier conditions but has the ability to be a larger and more vigorous plant with sufficient water and partial shade. The blossoms are tolerant to rain, not turning brown and rotting after a day or so of straight rain. 'Beky' buds early and is consistent with a large and long lasting blossom than many other cultivars known to the inventor.

On average, the plant itself can get to over 324 millimeters tall, not including the stem or flower. The free branching nature of 'Beky' allows the plants girth to grow and flourish. The width of a single plant is measured to be 563 millimeters and growing. The vibrancy of blossom color and strong green leaf color separates itself from any other known to the inventor. The semi-double blossom is a dark purple/violet with a darker edge to each petal. 'Beky's' stem is a distinguished light green, while the leaf produces a unique variation of colors all in its own. 'Beky's' standout performance is regarded highly due to its excellent growth habit, size, blossom and leaf.

The new cultivar of the present invention is being marketed under the BARTLETT'S trademark.

BRIEF DESCRIPTION OF THE PHOTOGRAPH

Accompanying this application is a photographed picture of the plant and its' aspects.

Figure 1:
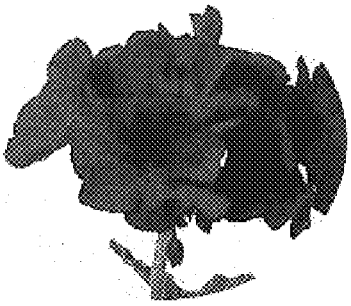

1. FIG. 1 shows the large, semi-double blossom and the purple to violet color described in the summary.

Figure 2:
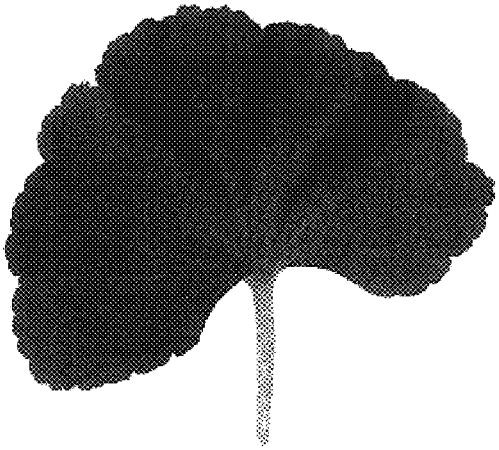

2. FIG. 2 enables us to see the medium green leaf with the medium green zone.

Figure 3:
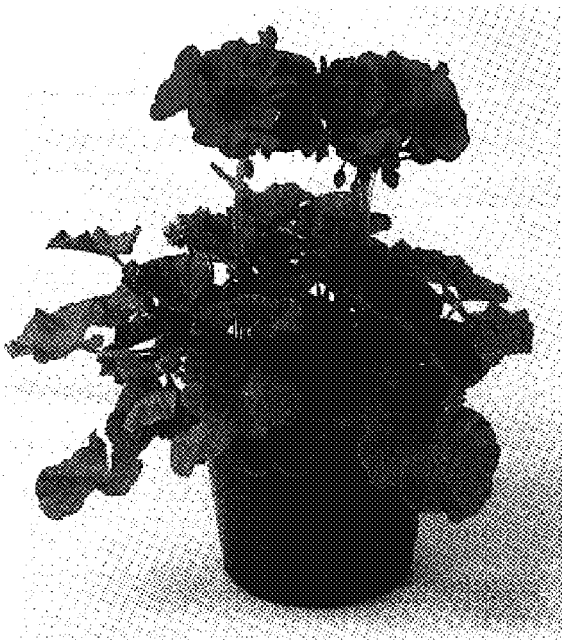

3. FIG. 3 shows the overall plant. This is a single plant from a cutting in a four-inch pot. The height, width, and growth habit are clearly seen here.

DETAILED BOTANICAL DESCRIPTION

The following observations and measurements describe asexual reproductions of 'Beky' grown in greenhouses located in Sudbury, Mass., USA. The plant history was taken on 3 month old plants grown in 7.5" pots, blossomed under natural light in a greenhouse and color readings were taken in the greenhouse in Sudbury, Mass. under ambient light. Color references are primarily to the Pantone Color Selector Chart 1000/coated 1995. The color values were determined on Oct. 22, 2003 under natural light conditions of 200 foot-candles.

Classification:

*Botanical.*—*Pelargonium×hortorum.*

*Variety denomination.*—'Beky'.

Inflorescence:

A. Umbel:

*Average diameter.*—Approximately 8.5 to 10.5 cm.

*Average depth.*—Approximately 4.75 to 6.5 cm.

*Peduncle length.*—Approximately 14 to 16 cm.

*Peduncle diameter.*—Approximately 0.15 to 0.25 cm.

*Pedicel length.*—Approximately 2.5 to3 cm.

*Number of umbels per plant.*—When grown in a 7.5" pot at 8 weeks after the sticking of a rooted cutting, there commonly are approximately 6 to 8 umbels per plant. The umbels form approximately 12 to 14 cm above the foliage.

*Number of florets per umbel.*—When grown in a 7.5" pot at 8 weeks, approximately 24 to 28 florets per umbel commonly are formed.

Flower depth: Approximately 4.2 to 5.7 cm.

B. Corolla:

*Buds.*—Elliptical to round in configuration, initially light green and changing to dark violet at the time of opening, and approximately 12 to 15 mm. in length and approximately 6 to 8 mm. in width.

*Average diameter.*—Approximately 5 to 7 cm.

*Form.*—Commonly semi-double with at least two petaloids.

*Petals.*—Spatulate shaped, satiny and smooth. Commonly approximately 6 to 8 petals are present per floret. Petal base is V-shaped with a semi-circular margin. Petal length is approximately 0.75 cm and diameter is approximately 0.25 cm. Upper petal surface is smooth as opposed to lower petal surface being slightly rougher.

*Number of petaloids.*—Commonly forms approximately 2 to 5 petaloids per floret. The petaloids are exactly the same as the petals excepting their diameter are approximately 0.05 cm.

*Color.*—General tonality from a distance of three meters: Dark Violet.

*Color of upper petal surface.*—Pantone 233C.

*Color of lower petal surface.*—Pantone 224C.

*Overall appearance of color.*—Pantone 237C.

*Markings of upper petals.*—Orange spot at base of petal Pantone 1787C.

*Sepals.*—5 to 7 sepals per floret with a length of approximately 0.3 to 0.7 cm and width of 0.04 to 0.08 cm. The overall shape is elliptical with V-shaped base and margin and semi-circular apex. Upper and lower surface are the same texture and color. Smooth, non-glossy with both Pantone.

C. Reproductive organs:

*Androecium.*—5 fertile anthers, with whitish filaments, orange pollen is located on the lower side of the mature (open) anther. The surface of the anther under the pollen is black.

*Gynoecium.*—5 lobed violet stigma, Pantone 233C, greenish style Pantone 374c; one pistil Pantone 370c per flower.

*Fertility and seed set.*—Commonly does not produce fruits in the absence of mechanical fertilization.

*Spring flowering response period.*—Approximately 5 to 8 weeks from rooted cuttings under standard greenhouse conditions.

*Outdoor flower production.*—Freely flowering under outdoor growing conditions with substantially continuous blooming.

*Flowering duration.*—The flowers last approximately 12 to 17 days under standard greenhouse conditions and they dehisce cleanly.

*Durability.*—Ships well.

*Pest/disease resistance/susceptibility.*—No susceptibility to pests or diseases noted to date. Disease resistance has not been tested to date.

Plant:

*A. Foliage.*—Medium green with slight zonation. Zoning color is Pantone 362c. The leaves are pubescent on the upper surface, and smooth on the lower surface.

*Length.*—3 to 4 cm.

*Width.*—5 to 6 cm.

*Form.*—Reniform, with a cordate base.

*Margin.*—Irregularly crenate.

*Ribs and veins.*—Palmate 5 to 6 cm. long.

*Leaf color.*—Upper side is Pantone 368C. Under side is Pantone 370C. Leaf upper surface covered predominately with trichomes Pantone 368c and leaf lower surface is predominately smooth.

*Petioles.*—Commonly approximately 3 to 6 cm long with a diameter of 0.02 to 0.06 cm. Petiole color is Pantone 370c.

A. General appearance and form:

*Internode length.*—Commonly varies from approximately 0.6 to 0.9 cm.

*Branching pattern.*—Freely basal branching as well as lateral branching. No pinching is required to obtain self-branching. A self-branching growth habit is observed in the absence of a growth regulator.

*Height.*—Approximately 20 to 26 cm. above a 7.5" pot at 8 weeks under standard greenhouse conditions.

It is claimed:

1. A new and distinct variety of *geranium* plant, as herein illustrated and described.

* * * * *